United States Patent [19]

Speranza et al.

[11] Patent Number: 5,324,838
[45] Date of Patent: Jun. 28, 1994

[54] BICYCLO[4.3.0]1,4,7-TRIAZANON-4-ENE-ONE USEFUL IN THE EXTRACTION OF PRECIOUS METALS

[75] Inventors: George P. Speranza; Martin J. Plishka, both of Austin, Tex.

[73] Assignee: Texaco Chemical Company, White Plains, N.Y.

[21] Appl. No.: 980,937

[22] Filed: Nov. 23, 1992

[51] Int. Cl.$^5$ ............................................ C07D 241/36
[52] U.S. Cl. ........................................ 544/350; 423/22
[58] Field of Search .......................................... 544/350

[56] References Cited

U.S. PATENT DOCUMENTS 4,578,386  3/1986  Lee ...................................... 514/241

OTHER PUBLICATIONS

C. J. Pedersen, "Cyclic Polyethers and Their Complexes with Metal Salts," *Journal of the American Chemical Society*, vol. 89, No. 26, Dec. 20, 1967, pp. 7017-7036.
O. Vogl, et al., "Polyoxamides I. Polymerization of Cyclic Diamides," *Macromolecules*, vol. 1, No. 4, Jul.-Aug., 1968, pp. 311-315.
O. Vogl, et al., "Polyoxamides. II. Polymerization of Cyclic Diamides," *Macromolecules*, vol. 1, No. 4, Jul.-Aug., 1968, pp. 315-318.
K. E. Krakowiak, et al., "Synthesis of Aza-Crown Ethers," *Chemical Reviews*, vol. 89, No. 4, 1989, pp. 929-972.
R. A. Lofquist, et al., "Hydrophilic Nylon for Improved Apparel Comfort," *Textile Research Journal*, Jun. 1985, p. 325-333.
L. Z. Chung, et al., "Block Copolyetheramides. II. Synthesis and Morphology of Nylon-6 Based Block Copolyetheramides," *J. Polym. Sci. Part A: Polym. Chem.*, vol. 30, 1992, pp. 951-953.

*Primary Examiner*—Nicholas S. Rizzo
*Attorney, Agent, or Firm*—James L. Bailey; Kenneth R. Priem; David L. Mossman

[57] ABSTRACT

Bicyclo[4.3.0]1,4,7-triazanony-6-ene-5-one may be made easily, in good yield and in one step by reacting diethyl oxalate with a diethylene triamine. The bicyclo[4.3.0]1,4,7-triazanon-6-ene-5-one material made by this process may be used to selectively separate metal ions from solution, or complexed together with a metal ion act as a catalyst. Surprisingly, related bicyclic triazines do not show the ability to complex with metal ions and precipitate them from solution.

1 Claim, No Drawings

BICYCLO[4.3.0]1,4,7-TRIAZANON-4-ENE-ONE USEFUL IN THE EXTRACTION OF PRECIOUS METALS

FIELD OF THE INVENTION

The invention relates to large organic ring structures and methods for making the same and, in one aspect, more particularly relates to bicyclo[4.3.0]1,4,7-triazanon-6-ene5-one, and methods for making and using the same.

BACKGROUND OF THE INVENTION

Large organic ring structures are known materials useful as chelating agents for selective binding and extraction of cations and as antioxidants. A number of other uses are recited in the recent review article by K. E. Krakowiak et al., "Synthesis of Aza-Crown Ethers," *Chemical Reviews*, Vol. 89, No. 4, 1989, pp. 929–972, including use as key intermediates in the synthesis of cryptands and other N-substituted ligands.

Unfortunately, previous routes to producing the diaza crown ethers are very tedious and expensive, as outlined in the K. E. Krakowiak et al. article. This publication notes that diaza crown ethers can be prepared by several different routes, for example, reacting 1,2-bis(2-haloethoxy)ethane or triethylene glycol ditosylates with triethylene glycol diamine or bis(tosylamides) followed by removal of the pendant tosyl groups, if required. Another route concerns reacting a secondary amine with a 1,2-bis(2-haloethoxy)ethane followed by removal of the pendant alkyl groups; or reacting triethylene glycol diamine with triglycolyl dichloride. A number of other methods are described.

C.J. Pedersen, "Cyclic Polyethers and Their Complexes with Metal Salts," *Journal of the American Chemical Society*, Vol. 89, No. 26, Dec. 20, 1967, pp. 7017-7036, describes the synthesis of 33 cyclic polyethers, derived from aromatic vicinal diols and containing 9 to 60 atoms including 3 to 20 oxygen atoms in the ring. Some of the compounds were prepared in good yields without the use of a high-dilution technique. Fifteen of the compounds have been catalytically hydrogenated to the corresponding saturated cyclic polyethers. Many of those containing 5 to 10 oxygen atoms form stable complexes with some or all of the cations of: Li, Na, NH$_4$, RNH$_3$, K, Rb, Cs, Ag(I), Au(I), Ca, Sr, na, Cd, Hg(I), Hg(II), La(III), Ti(I), Ce(III) and Pb(II). Many of these complexes could be isolated in the crystalline form depending on the anion. They appeared to be salt-polyether complexes formed by ion-dipole interaction between the cation and the negatively charged oxygen atoms of the polyether ring. The stoichiometry of the complexes is one molecule of polyether per single ion regardless of the valence. Some of the polyethers, by complexing, solubilize inorganic compounds, such as potassium hydroxide and permanganate, in aromatic hydrocarbons.

The preparation of cyclic dioxamides has been studied in 0. Vogl, et al., "Polyoxamides. I. Polymerization of Cyclic Diamides," *Macromolecules*, Vol. 1, No. 4, July-August, 1968, pp. 311–315. After reviewing all the methods available to them, they chose the high dilution method using oxalyl chloride and diamine. Even though the high dilution technique was used, their yields of cyclic oxamide were very low. Attempts to prepare the cyclics from ethyl (or methyl) oxalate and hexamethylenediamine hydrochloride directly failed. Also of interest is 0. Vogl, et al., "Polyoxamides. II. Polymerization of Cyclic Diamides," *Macromolecules*, Vol. 1, No. 4, July–August, 1968, pp. 315–318.

Certain oxamides are set out in R. M. Izatt, et al., "Thermodynamic and Kinetic Data for Macrocycle Interaction with Cations and Artions," *Chem. Rev.*, 1991, pp. 1721-1777, but the unique oxamides of the present invention are not set forth.

As may be seen by reviewing the above-noted preparations, macrocyclic oxamides prepared by conventional methods often require more than one step, high dilution conditions and more than one reagent. All of these considerations increase the cost of the produced cyclic oxamides. Note that the Pedersen article discusses the desirability of avoiding high dilution techniques; Vogl, et al. were unable to avoid them. It would be desirable if cyclic materials having use as selective complexing agents could be prepared by a one-step procedure which did not require high dilution.

SUMMARY OF THE INVENTION

The original objective of this work was to prepare macrocyclic amides from diethylene triamine and oxalic derivatives, as supposed by the following reaction:

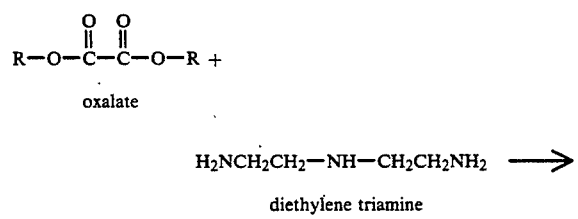

where R is hydrogen or alkyl

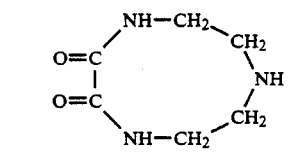

or

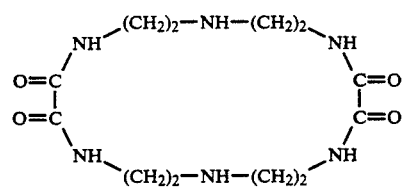

or even

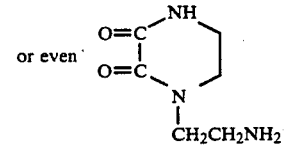

Such compounds would give reactive nitrogen groups for reaction into other molecules. Instead, the reaction took a surprising course.

Accordingly, it is an object of the present invention to provide a simplified one-step procedure for synthesizing bicyclic triazines from readily available chemicals.

It is another object of the present invention to provide a method for the preparation of bicyclic triazines that does not require high dilutions.

Another object of the invention is to provide novel bicyclic triazines.

In carrying out these and other objects of the invention, there is provided, in one form, bicyclo[4.3.0]1,4,7-triazanon-6-ene-5-one having the structure:

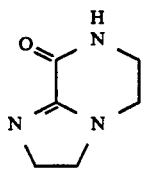

DETAILED DESCRIPTION OF THE INVENTION

It has been discovered that bicyclo[4.3.011 4 7 triazanon-6-ene-5-one may be made simply and in one step and Sood yield by reactin; oxalic acid, dialkyl oxalates or esters thereof with diethylene triamine. The reactants used are relatively low cost raw materials. The material may be represented by the structure:

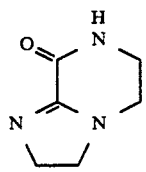

It will be understood that this structure encompasses the equilibrium condition represented by:

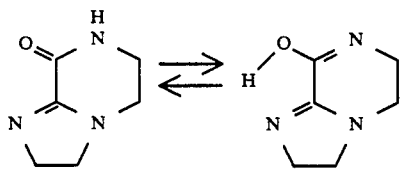

That this compound was obtained rather than any of the three shown with respect to this reaction schematically illustrated previously is quite surprising. It is further surprising that while reactions using related compounds such as dipropyl triamine and diethyl malonate give triazines, these structurally related triazines do not selectively complex with metal ions. In this invention, oxalic acid, esters thereof and half esters of oxalic acid are useful to be reacted with diethylene triamine. Dialkyl oxalates, and particularly diethyl oxalate and its esters are preferred.

Surprisingly, the preferred procedure can be carried out in one step without resorting to high dilution techniques. Given the teachings of Vogl, et al., described above, that oxamides are not produced in one step by reacting ethyl (or methyl) oxalate and hexamethylenediamine hydrochloride, the present inventive process is particularly unexpected. Yields up to about 90% or more are obtained. Additionally, the reaction can be scaled to the preparation of large quantities of material.

Bicyclo[4.3.0]1,4,7-triazanon-6-ene-5-one itself is an excellent complexing agent for metallic ions making it useful in procedures for separating and removing certain metals from solutions containing other metal ions.

It is anticipated that bycyclo[4.3.011,4,7-triazanon-6-ene-5-one of this invention would be useful as in catalysts for organic reactions.

The process involves reacting an oxalate or its ester, preferably diethyl oxalate, with a diethylene triamine at a temperature between about 0 and 200° C., at a pressure between subatmospheric and about 200 psi, and in a solvent selected from the group consisting of isopropanol, 2-ethylhexanol, diglyme, triglyme, methanol, ethanol, N-methylpyrrolidone, and the like. Isopropanol is a preferred solvent; it is relatively nontoxic and is low in cost. In short, the solvent should be one which is inert (i.e., does not react with the triamine or the oxalic compound). Preferably, the reaction temperature is between about 20 and about 180 ° C. while the pressure is preferably atmospheric. No catalyst is required for the inventive reaction. As will be evident, the molar ratio of diethyl oxalate to diethylene triamine will be about 1:1.

As will be demonstrated, bicyclo[4.3.0]1,4,7-triazanon-6-ene-5-one of this invention is a good selective agent for metallic ions and are thus useful for separating and removing metals from solutions. The exact amount of bicyclo[4.3.0]1,4,7-triazanon6-ene5-one which may be used can readily be determined by one of skill in the art and any amount which removes metal ions to a measurable extent is considered an effective amount. Generally, each molecule will remove about one metal ion as is customary in this art. In one embodiment, the treatment level should range from about 2 to about 1000 ppm. This material has been useful to extract salts of platinum, silver, gold, rhodium, molybdenum, chromium, lead, palladium and cesium from aqueous solutions into solid complexes.

Bicyclo[4.3.0]1,4,7-triazanon-6-ene-5-one and the methods for preparing and using it will now be further illustrated with certain examples, which are meant to illuminate but not necessarily limit the claimed invention. Product molecular weights were characterized with a Kratos magnetic sector mass spectrometer. A solid probe operating in an electron impact mode was employed.

EXAMPLE 1

Diethyl oxalate and diethylene triamine

To a one liter, three-necked flask equipped with a stirrer and two dropping funnels was added 300 mi. of isopropanol. The isopropanol was heated to boiling and from one dropping funnel was added 31 g of diethylene triamine in 120 ml of isopropanol. At the same time, 44 g of diethyl oxalate in 120 ml of isopropanol was added from the other funnel. The simultaneous addition took place over a four-hour period. Solids deposited. The contents were heated at reflux (84° C.) for an additional two hours. The solution was cooled to room temperature and the solids filtered and dried (43.7 g). Melting point history of the white solid:

185° C.—gained some color,
200° C.—turning tan,
210° C.—light brown,
230° C.—red brown,
20 236° C.—brown.

Amine analysis on titration with p-toluenesulfonic acid - 5.85 meg/g. Mass spectroscopy showed molecular weight of 139. The following structure was determined:

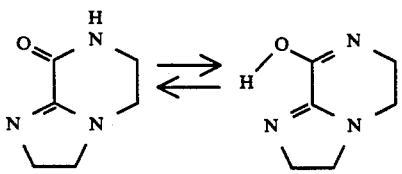

1.001 g was sublimed at 212° C., 0.03 mmHg. 0.143 g of solid and 0.811 g of polymeric material was obtained.

The bicyclo[4.3.0]1,4,7-triazanon-6-ene-5-one recovered was insoluble in hot methanol, hot ethanol, hot acetone and hot cyclohexane. It appeared to be soluble in water and dimethylformamide, but considerable haze was present.

EXAMPLE 1A

Use of Bicyclo[4.3.0]1,4,7-triazanon-6-ene5-one

The bicyclo[4.3.011,4,7-triazanon-6-ene-5-one prepared in Example 1 removed all of the following cations from an acidic aqueous solution by forming either a white or colored precipitate. Typically, 1.00 g of bicyclo-4.3.0]1,4,7-triazanon-6-ene-5-one was dissolved in an aqueous 2% HCl solution and 100 ml of 100 ppm metal was added. A precipitate usually formed within minutes; some took several hours.

| | | |
|---|---|---|
| 1. | Molybdenum (from Mo catalyst for oxidation of propylene to propylene oxide) | Blue precipitate. |
| 2. | Chromium | Bluish-white precipitate. |
| 3. | Lead | White precipitate. |
| 4. | Gold | Gold-colored precipitate. |
| 5. | Palladium | Golden precipitate. |
| 6. | Rhodium | Pinkish precipitate. |
| 7. | Uranium | White precipitate. |
| 8. | Silver | White precipitate. |
| 9. | Platinum | Yellowish precipitate. |

No precipitate formed with calcium.

EXAMPLE 2

Diethyl Oxalate and Diethylene Triamine

To a one liter three-necked flask equipped with a stirrer, thermometer, dropping funnel and condenser was charged 300 ml of isopropanol and 146 g of diethyl oxalate. Then, 104 g. of diethylene triamine was slowly added, keeping the temperature between 20 and 32° C. with cooling. The addition took place over about a three-hour period. The contents were stirred for two hours at 30%. and a portion of the solids which precipitated were collected and dried. The rest was heated at reflux temperature for three hours (83° C.). A viscous solution resulted, so 150 ml of isopropanol was added. The contents were cooled to ice-water temperature and the white crystals separated and dried in a vacuum dessicator at 60–65° C. and 0.15 mmHg. The final product weighed 152.1 g.

The two samples were very similar when analyzed by mass spectroscopy. The bulk of the sample appeared to be the bicyclic amide of molecular weight 139 and/or a substituted piperazine. The 139 peak predominates on early heating, but subsequently fragmentation takes place on further heating showing largely a peak with a molecular weight of 99.

The instability of the product was also demonstrated in earlier melting point observations and in the sublimation studies.

COMPARATIVE EXAMPLE 3

Diethyl Oxalate and Dipropylene Triamine

To a one liter, 3-necked flask equipped with a stirrer, thermometer and two dropping funnels was charged 300 ml. of isopropanol. One addition funnel contained 73 g of diethyl oxalate and 100 ml of isopropanol. The second contained 64.5 g of dipropylene triamine and 100 ml of isopropanol. They were added simultaneously over a three-hour period with the temperature maintained around 29° C. The contents were heated to reflux and held for five hours. The solids obtained on cooling were dried: weight 55.8 g. Mass spectroscopy probe technique resulted in the following. The sample consisted of several different components. The two main components appeared to be polymer and the bicyclic amides of molecular weight 167. Also present was the cyclic dimer; molecular weight of 370 and possibly a small amount of cyclic monomer, molecular weight 185 as shown below. The product obtained did not precipitate palladium.

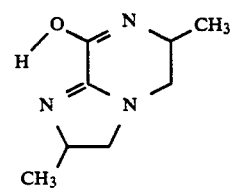

MW = 167

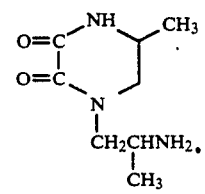

MW = 185

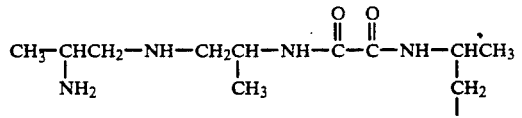

MW = 270

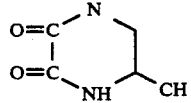

COMPARATIVE EXAMPLE 4

Diethyl Oxalate and Aminoethyl Ethanolamine

Equal molar amounts of aminoethyl ethanolamine and diethyl oxalate (104 g and 146 g, respectively) in isopropanol were added simultaneously to boiling isopropanol as described in Example 1. The addition took place over a three-hour period. Hard cake was obtained which was dried to give 112.3 g of dried solids. The product was very soluble in water and mass spectroscopy revealed that the bulk of the material was as shown below. It did not form a precipitate with palladium salts.

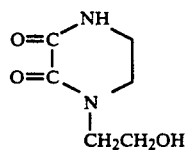

COMPARATIVE EXAMPLE 5

Diethyl Malonate and Diethylene Triamine

To a one-liter, three-necked flask equipped with a thermometer, two dropping funnels, stirrer and condenser was added 300 ml of 2-ethylhexanol which was heated to boiling at 182° C. In one dropping funnel was placed 80 g of diethyl malonate and 100 ml of 2-ethylhexanol. The second funnel had 52 g of DETA and 130 ml of 2-ethylhexanol. The two solutions were added over a three hour period. On standing overnight, no crystals were obtained. The 2-ethylhexanol was removed and 77.4 g of product was obtained which was very viscous. Results of probe mass spectroscopy showed that the bulk of the sample was made up of two components. The first appeared to be the bicyclic material with molecular weight of 153 which corresponds to the formula I. The other product appeared to have a molecular weight of 169 which corresponds to structure II.

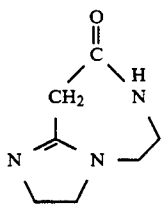

I

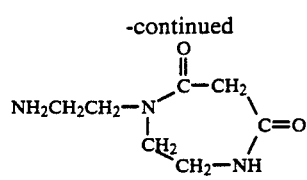

II

The product was soluble in water and did not form a precipitate with palladium.

COMPARATIVE EXAMPLE 6

Diethyl Oxalate and Triethylene Tetramine

To a one-liter, three-necked flask equipped with a stirrer, thermometer, condenser and two dropping funnels was added 300 ml of isopropanol. The isopropanol was heated to boiling. One dropping funnel contained 29.2 g of diethyl oxalate and 120 ml of isopropanol. The second contained 29.2 g of triethylene tetramine and 120 ml of isopropanol. The reactants were added over a four-hour period at the same rate to the boiling isopropanol. Crystals that formed stuck very lightly to the flask. The solids were dried to give 29.0 g of product. The product material did not form a precipitate. with palladium salts.

Many modifications may be made in the process of this invention without departing from the spirit and scope thereof which are defined only in the appended claims. For example, one skilled in the art may discover that bicyclo[4 30]1,4,7-triazanon-6-ene-5-one has utility for other uses, or that bicyclo[4.3.01l,4,7-triazanon-6-ene-5-one can be made by other ways.

We claim;

1. Bicyclo[4.3.0]1,4,7-triazanon-6-ene-5-one having the structure:

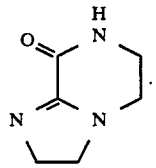

* * * * *